US007009068B2

(12) United States Patent
Schmutzler et al.

(10) Patent No.: US 7,009,068 B2
(45) Date of Patent: Mar. 7, 2006

(54) PHOSPHITE COMPOUNDS AND THE METAL COMPLEXES THEREOF

(75) Inventors: Reinhard Schmutzler, Wolfenbuettel (DE); Ion Neda, Braunschweig (DE); Christine Kunze, Vordorf (DE); Armin Börner, Rostock (DE); Detlef Selent, Berlin (DE); Cornelia Borgmann, Recklinghausen (DE); Dieter Hess, Marl (DE); Klaus-Diether Wiese, Haltern (DE)

(73) Assignee: Oxeno Olefinchemie GmbH, Marl (DE)

( * ) Notice: Subject to any disclaimer, the term of this patent is extended or adjusted under 35 U.S.C. 154(b) by 9 days.

(21) Appl. No.: 10/485,817

(22) PCT Filed: Aug. 7, 2002

(86) PCT No.: PCT/EP02/08798

§ 371 (c)(1),
(2), (4) Date: Jun. 15, 2004

(87) PCT Pub. No.: WO03/016320

PCT Pub. Date: Feb. 27, 2003

(65) Prior Publication Data

US 2004/0236134 A1    Nov. 25, 2004

(30) Foreign Application Priority Data

Aug. 16, 2001   (DE) .................................. 101 40 083

(51) Int. Cl.
C07F 9/02   (2006.01)
(52) U.S. Cl. ............................. 558/153; 558/77; 558/78
(58) Field of Classification Search ............... 558/153, 558/77, 78; 502/104
See application file for complete search history.

(56) References Cited

U.S. PATENT DOCUMENTS

| 4,668,651 A | 5/1987 | Billig et al. |
| 4,748,261 A | 5/1988 | Billig et al. |
| 4,885,401 A | 12/1989 | Billig et al. |
| 5,312,996 A | 5/1994 | Packett |

FOREIGN PATENT DOCUMENTS

| EP | 214 622 | 3/1987 |
| EP | 472 071 | 2/1992 |
| EP | 1 201 675 | 5/2002 |
| EP | 1201675 | 5/2002 |

OTHER PUBLICATIONS

Kunze C et al: "Calix(4)Arene-Based Bis-Phosphonites, Bis-Phosphites, and Bis-O-Acyl-Phosphites as Ligands in the Rhodium (I)-Catalyzed Hydroformylation of 1-Octene" Zeitschrift Fuer Anorganishe Und Allgemeine Chemie, Verlag Von Leopold Voss, Leipzig, DE, vol. 628, No. 4, 2002, pp. 779-787, XP008010119 ISSN: 0044-2313 the whole document.

Shadid et al., {The Synthesis of Cytokinin Phosphates, Tetrahedron (1990), 46 (3), 901-912}.*

Selent et al., {New Phosphorus Ligands for the Rhodium-Catalyzed Isomerization/Hydroformylation of Internal Octenes, Angew. Chem. Int. Ed. 40 (9), 1696-1698, 2001}.*

Siedentop et al., {The Synthesis and Complexation of Spacer Modified Phosphorylated Glucose Derivatives, Z. Naturfosch, 55 b, 956-960, (2000)}.*

Siedentop T. et al.: "Synthese und Komplexierung phosphorylierte spacer-modifizierter Glucosederivate" Zeitschrift Fur Naturforschung, Teil B: Anorganische Chemie, Organische Chemie., vol. 55, No. 10, -Oct. 2000 pp. 956-960, XP 002223607 Verlag Der Zeitschrift Fur Naturforschung, Tubingen., DE ISSN: 0932-0776 Schema 2 und Seite 959, Darstellung von 7.

Selent D et al: "New Phosphorus Ligands For The Rhodium-Catalyzed Isomerization/Hydroformylation of Internal Octenes" Angewandte Chemie.International Edition, Verlag Chemie. Weinheim, DE, vol. 40, No. 9, May 4, 2001, pp. 1696-1698, XP001009251 ISSN: 0570-0833 the whole document.

(Continued)

*Primary Examiner*—Johann Richter
*Assistant Examiner*—Chukwuma Nwaonicha
(74) *Attorney, Agent, or Firm*—Oblon, Spivak, McClelland, Maier & Neustadt, P.C.

(57) ABSTRACT

Phosphites of the formula I or II

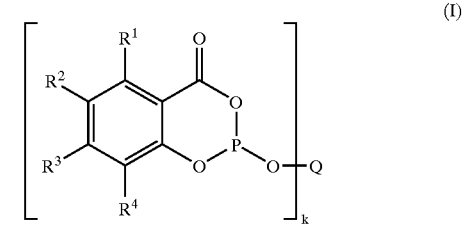

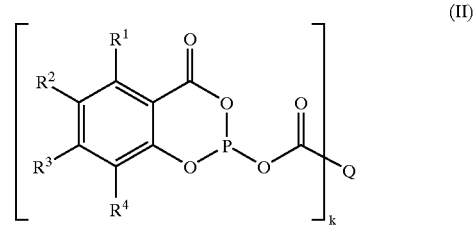

and their metal complexes, their preparation and the use of the phosphites as ligands in catalytic reactions, in particular in processes for the hydroformylation of olefins, are described.

30 Claims, No Drawings

OTHER PUBLICATIONS

Siedentop T. et al.: "Synthese und Komplexierung phosphorylierter spacer-modifizierter Glucosederivate" Zeitschrift Fur Naturforschung, Teil B: Anorganische Chemie, Organische Chemie., vol. 55, No. 10, Oct. 2000 pp. 956-960, XP 002223607 Verlag Der Zeitschrift Fur Naturforschung. Tubingen., DE ISSN: 0932-0776 Schema 2 und Seite 959, Darstellung von 7.

Selent D et al: "New Phosphorus Ligands for the Rhodium-Catalyzed Isomerization/Hydroformylation of Internal Octenes" Angewandte Chemie, International Edition, Verlag Chemie. Weinheim, DE, vol. 40, No. 9, May 4, 2001, pp. 1696-1698, XP001009251 ISSN: 0570-0833 the whole document.

Kunze C et al: "Calix(4)Arene-Based Bis-Phosphonites, Bis-Phosphites, and Bis-O-Acyl-Phosphites as Ligands in the Rhodium (I)-Catalyzed Hydroformylation of 1-Octene" Zeitschrift Fuer Anorganische Und Allgemeine Chemie, Verlag Von Leopold Voss, Leipzig, DE, vol. 628, No. 4, 2002, pp. 779-787, XP008010119 ISSN: 0044-2313 the whole document.

* cited by examiner

PHOSPHITE COMPOUNDS AND THE METAL COMPLEXES THEREOF

The present invention relates to phosphites and their metal complexes, and the preparation and the use of the phosphites as ligands in catalytic reactions.

The reactions between olefin compounds, carbon monoxide and hydrogen in the presence of a catalyst to form the aldehydes having one more carbon atom is known as hydroformylation (oxo process). As catalysts in these reactions, use is frequently made of compounds of the transition metals of groups 8 to 10 of the Periodic Table of the Elements, in particular compounds of rhodium and of cobalt. Compared to catalysis by cobalt compounds, the hydroformylation using rhodium compounds generally offers the advantage of higher selectivity and is thus usually more economical. In the case of the rhodium-catalyzed hydroformylation, use is usually made of complexes comprising rhodium and preferably trivalent phosphorus compounds as ligands. Known ligands are, for example, compounds from the classes of phosphines, phosphites and phosphonites. An overview of hydroformylation of olefins may be found in B. CORNILS, W. A. HERRMANN, "Applied Homogeneous Catalysis with Organometallic Compounds", Vol. 1&2, VCH, Weinheim, N.Y., 1996.

Each catalyst system (cobalt or rhodium) has its specific advantages. Depending on the starting material and target product, different catalyst systems are used. If rhodium and triphenylphosphine are employed, α-olefins can be hydroformylated at relatively low pressures. An excess of triphenylphosphine is generally used as phosphorus-containing ligand; a high ligand/rhodium ratio is necessary to increase the selectivity of the reaction giving the commercially desired n-aldehyde product.

U.S. Pat. Nos. 4,694,109 and 4,879,416 relate to bisphosphine ligands and their use in the hydroformylation of olefins at low synthesis gas pressures. Particularly in the hydroformylation of propene, high activities and high n/i selectivities are achieved using ligands of this type.

WO-A-95/30680 describes bidentate phosphine ligands and their use in catalysis, including in hydroformylation reactions.

Ferrocene-bridged bisphosphines are disclosed, for example, in U.S. Pat. Nos. 4,169,861, 4,201,714 and 4,193,943 as ligands for hydroformylations.

Selent D. et al, Angewandte Chemie, International Edition, volume 40, No. 9, WILEY-VCH Verlag GmbH, Weinheim 2001, pages 1696 to 1698 discloses biphosphite ligands containing a phosphorinone structural unit and their use for hydroformylation catalysts.

A disadvantage of bidentate phosphine ligands is their relatively complicated preparation. It is therefore often not economically viable to use such systems in industrial processes.

Rhodium-monophosphite complexes are suitable catalysts for the hydroformylation of branched olefins having internal double bonds, but the selectivity for terminally hydroformylated compounds is low. EP-A-0 155 508 discloses the use of bisarylene-substituted monophosphites in the rhodium-catalyzed hydroformylation of sterically hindered olefins, e.g. isobutene.

Rhodium-bisphosphite complexes catalyze the hydroformylation of linear olefins having terminal and internal double bonds to give predominantly terminally hydroformylated products, while branched olefins having internal double bonds are reacted to only a small extent. On coordination to a transition metal center, these phosphites give catalysts of increased activity, but the operating life of these catalyst systems is unsatisfactory, partly because of the hydrolysis sensitivity of the phosphite ligands. The use of substituted bisaryl diols as starting materials for the phosphite ligands, as described in EP-A-0 214 622 or EP-A-0 472 071, has enabled considerable improvements to be achieved.

According to the literature, the rhodium complexes of these ligands are extremely active hydroformylation catalysts for α-olefins. U.S. Pat. Nos. 4,668,651, 4,748,261 and 4,885,401 describe polyphosphite ligands by means of which α-olefins and also 2-butene can be converted with high selectivity into the terminally hydroformylated products. In U.S. Pat. No. 5,312,996, bidentate ligands of this type are also used for the hydroformylation of butadiene.

Although the bisphosphites mentioned are good complexing ligands for rhodium hydroformylation catalysts, it is desirable to develop new types of readily preparable phosphites to further improve their effectiveness, for example in hydroformylation.

It has surprisingly been found that novel phosphites of the structural formula I or II,

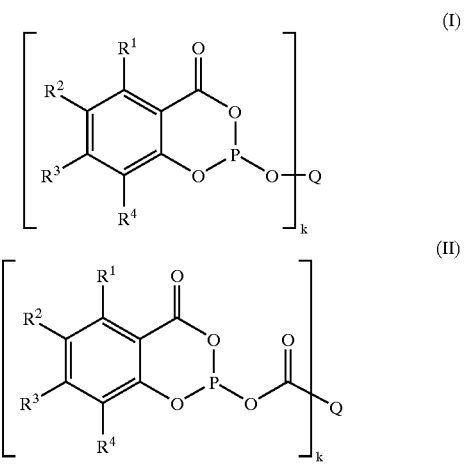

where $R^1$, $R^2$, $R^3$ and $R^4$ are each selected independently from among monovalent substituted or unsubstituted aliphatic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, H, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$, —$N=CR^9R^{10}$, where $R^9$ and $R^{10}$ are selected independently from among H, monovalent substituted or unsubstituted aliphatic and aromatic hydrocarbon radicals having from 1 to 25 carbon atoms and M is an alkali metal ion, formally half an alkaline earth metal ion, an ammonium ion or phosphonium ion, or adjacent radicals $R^1$ to $R^4$ together form a fused substituted or unsubstituted aromatic, heteroaromatic, aliphatic, mixed aromatic-aliphatic or mixed heteroaromatic-aliphatic ring system;

Q is a k-valent substituted or unsubstituted aliphatic, alicyclic, mixed aliphatic-alicyclic, heterocyclic, mixed aliphatic-heterocyclic, aromatic, mixed aliphatic-aromatic hydrocarbon radical having from 1 to 50 carbon atoms, where aliphatic parts of Q may contain oxygen, sulfur and/or nitrogen, k is at least 2 and $R^1$, $R^2$, $R^3$ and $R^4$ in the individual structural elements bound to Q can be different from one another, are suitable complexing ligands. If the radicals $R^1$ to $R^4$ in the individual structural elements bound to Q are different from one another, the phosphite is unsymmetrical.

The invention also provides complexes of the phosphite ligands with a metal of group 4, 5, 6, 7, 8, 9 or 10 of the Periodic Table of the Elements and their preparation.

The present invention further provides for the use of the phosphites and the phosphite-metal complexes in catalysis, preferably in homogeneous catalysis, in particular in the hydroformylation of olefins.

Further aspects of the invention are a process for the hydroformylation of olefins and a process for preparing the phosphite ligands.

In preferred phosphites of the formula I or II, at least two adjacent radicals $R^1$ to $R^4$ together form a fused aromatic, heteroaromatic, aliphatic, mixed aromatic-aliphatic or mixed heteroaromatic-aliphatic ring system which is unsubstituted or is substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, F, Cl, Br, I, —$CF_3$, —$CH_2(CF_2)_j CF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —N=$CR^9R^{10}$, where $R^9$, $R^{10}$ and M are as defined above.

In the phosphites of the formula I or II, Q is preferably a divalent to tetravalent radical. For example, Q can have a structure as shown in formula III,

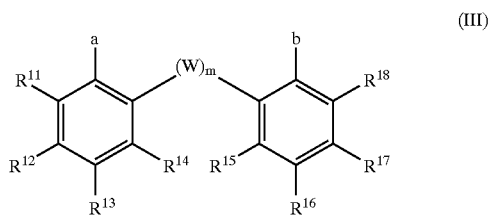

(III)

where $R^{11}$, $R^{12}$, $R^{13}$, $R^{14}$, $R^{15}$, $R^{16}$, $R^{17}$ and $R^{18}$ are as defined for $R^1$ to $R^4$ in claim 1 or 2, W is the divalent radical $CR^{19}R^{20}$, where $R^{19}$ and $R^{20}$ are as defined for $R^9$ and $R^{10}$, m=0–1 and the positions a and b represent the linkage points. Adjacent radicals $R^{11}$ to $R^{18}$ may, in a manner analogous to $R^1$ to $R^4$ in formula (I) or (II), together form a fused substituted or unsubstituted aromatic, heteroaromatic, aliphatic, mixed aromatic-aliphatic or mixed heteroaromatic-aliphatic ring system. The ring system is preferably substituted by at least one radical selected from among aliphatic, alicyclic, aromatic, heteroaromatic, mixed aliphatic-alicyclic, mixed aliphatic-aromatic, heterocyclic, mixed aliphatic-heterocyclic hydrocarbon radicals having from 1 to 50 carbon atoms, F, Cl, Br, I, —$CF_3$, —$CH_2(CF_2)_j CF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —N=$CR^9R^{10}$, where $R^9$, $R^{10}$ and M are as defined above.

Other examples of Q are a phenyl radical, a naphthyl radical, a bisaryl radical, a radical of a diphenyl ether or a calix[n]arene radical having the structure corresponding to the formula IV:

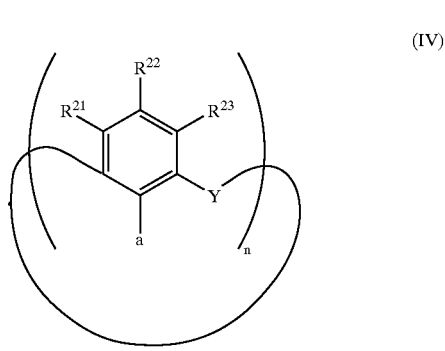

(IV)

where $R^{21}$, $R^{22}$ and $R^{23}$ are selected independently from among substituted or unsubstituted aliphatic and aromatic hydrocarbon radicals having from 1 to 25 carbon atoms, H, F, Cl, Br, I, —$CF_3$, —$CH_2(CF_2)_j CF_3$ where j=0–9, —$OR^{24}$, —$COR^{24}$, —$CO_2R^{24}$, —$CO_2M$, —$SR^{24}$, —$SO_2R^{24}$, —$SOR^{24}$, —$SO_3R^{24}$, —$SO_3M$, —$SO_2NR^{24}R^{25}$, —$NR^{24}R^{25}$ and —N=$CR^{24}R^{25}$, where $R^{24}$ and $R^{25}$ are as defined for $R^9$ and $R^{10}$ and M is an alkali metal ion, formally half an alkaline earth metal ion, an ammonium ion or phosphonium ion, or adjacent radicals $R^{21}$ to $R^{23}$ together form a fused substituted or unsubstituted aromatic, heteroaromatic, aliphatic, mixed aromatic-aliphatic or mixed heteroaromatic-aliphatic ring system; Y is the divalent radical $CR^{24}R^{25}$ or $CR^{24}R^{25}$—O—$CR^{24}R^{25}$; n=3–6 and the positions a represent the linkage points or are occupied by $OR^{24}$, where $R^{24}$ and $R^{25}$ are as defined above.

Representative phosphite ligands of the formula I or II are:

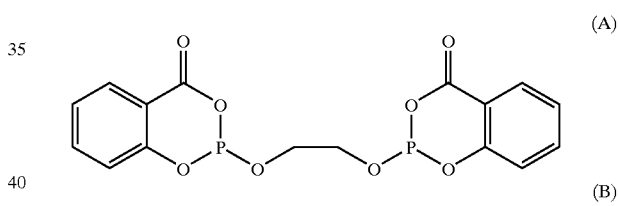

(A)

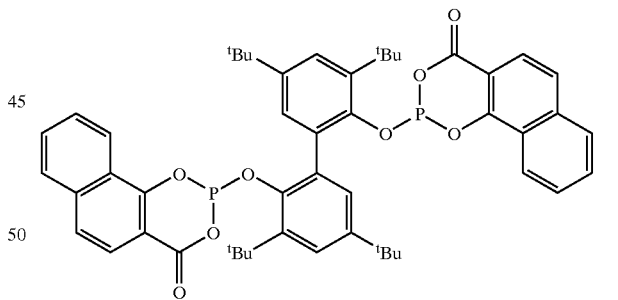

(B)

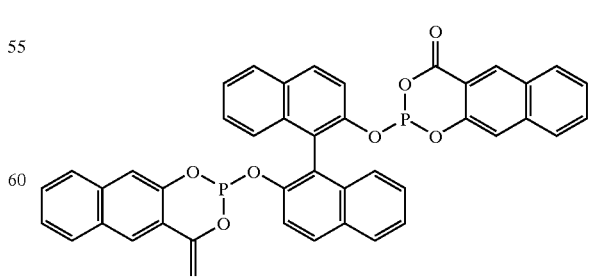

(C)

-continued

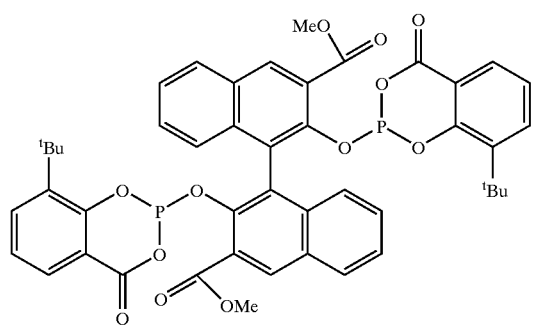
(D)

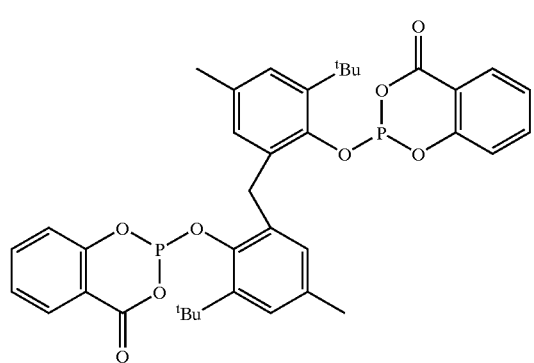
(E)

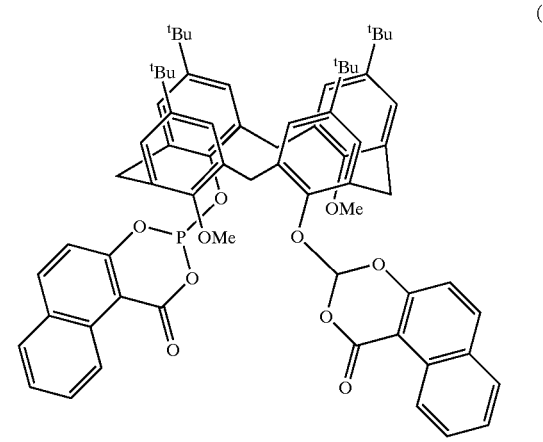
(F)

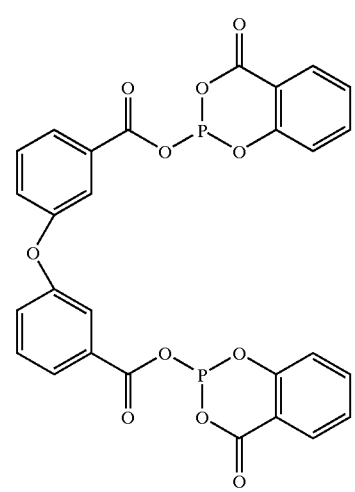
(G)

-continued (H)
(I)
(K)
(L)
(M)

The examples (I) to (M) are unsymmetrical phosphites.

The phosphites for the use according to the invention can be prepared from phosphorus-halides by means of a sequence of reactions with alcohols, carboxylic acids and/or α-hydroxyarylcarboxylic acids in which the halogen atoms on the phosphorus are replaced by oxygen groups. One of a number of possibilities for preparing the phosphites of the invention is the following synthetic route for bisphosphites:

In a first step, an α-hydroxyarylcarboxylic acid (1) is reacted with a phosphorus trihalide $PX_3$, e.g. $PCl_3$, $PBr_3$ and $PI_3$, preferably phosphorus trichloride $PCl_3$, in the presence of a base which is preferably used in equivalent or catalytic amounts to form a halodioxaphosphorinone (2).

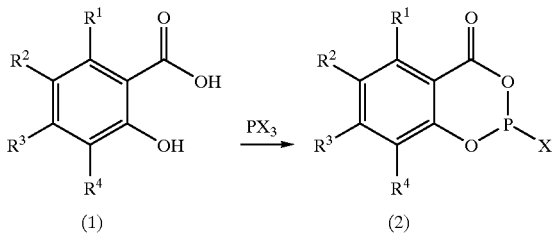

In a second reaction step, the halodioxaphosphorinone (2) is reacted with a diol (HO-Q-OH) or a dicarboxylic acid (HOOC-Q-COOH) in the presence of a base which is preferably used in equivalent or catalytic amounts to give the desired phosphite (I) or (II).

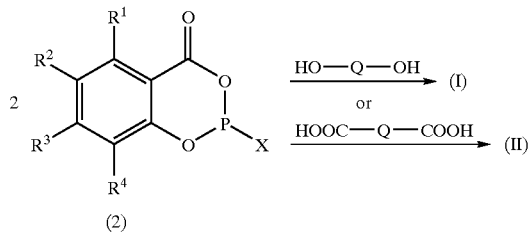

The radicals $R^1$ to $R^4$ and Q are as defined above.

In the synthesis of unsymmetrical bisphosphites, two differently substituted chlorodioxaphosphorinones (2a) and (2b) in which at least one radical $R^1$ to $R^4$ and (2b) has a different meaning in (2a) are prepared in the first reaction step and these are then, in the second reaction step, reacted in succession with the diol or the dicarboxylic acid in the presence of a base which is preferably used in equivalent or catalytic amounts.

Since the diols or dicarboxylic acids used and their downstream products are frequently solid, the reactions are generally carried out in solvents. Solvents used are aprotic solvents which react neither with the diols nor dicarboxylic acids nor with the phosphorus compounds. Examples of suitable solvents are tetrahydrofuran, ethers, such as diethyl ether or MTBE (methyl tert-butyl ether) and aromatic hydrocarbons such as toluene.

The reaction of phosphorus-halides with alcohols forms hydrogen halide which is bound by added bases. Examples of bases which can be used for this purpose are tertiary amines such as triethylamine, pyridine or N-methylpyrrolidinone. It may also be useful to convert the alcohols into metal alkoxides prior to the reaction, for example by reacting them with sodium hydride or butyllithium.

The phosphites are suitable ligands for the complexation of metals of groups 4, 5, 6, 7, 8, 9 and 10 of the Periodic Table of the Elements. The complexes can contain one or more phosphite ligands and, if desired, further ligands and are suitable as catalysts, preferably in homogeneous catalysis. Examples of suitable metals are rhodium, cobalt, iridium, nickel, palladium, platinum, iron, ruthenium, osmium, chromium, molybdenum and tungsten. Particularly in the case of metals of group 8, 9 or 10, the resulting complexes can be used as catalysts for hydroformylation, carbonylation, hydrogenation and hydrocyanation reactions; particular preference is given to rhodium, cobalt, nickel, platinum and ruthenium. For example, the use of rhodium in particular as catalyst metal gives high catalytic activities in hydroformylation reactions. The catalyst metals are used in the form of salts or complexes, in the case of rhodium, for example, rhodium carbonyls, rhodium nitrate, rhodium chloride, $Rh(CO)_2(acac)$ (acac—acetyl acetonate), rhodium acetate, rhodium octanoate or rhodium nonanoate.

The active catalyst species for the homogeneous catalysis are formed from the phosphite ligands of the invention and the catalyst metal under the reaction conditions, for instance in the case of hydroformylation a carbonylhydridophosphite complex on contact with synthesis gas. The phosphites and any further ligands can be introduced into the reaction mixture in free form together with the catalyst metal (as salt or complex) in order to generate the active catalyst species in situ. It is also possible to use a phosphite-metal complex comprising the above mentioned phosphite ligands and the catalyst metal as precursor for the actual catalytically active complex. These phosphite-metal complexes are prepared by reacting the appropriate catalyst metal of groups 4 to 10 in elemental form or in the form of a chemical compound with the phosphite ligand.

As additional ligands present in the reaction mixture, it is possible to use phosphorus-containing ligands, for example phosphines, phosphites, phosphonites or phosphinites.

Examples of such ligands are:

phosphines: triphenylphosphine, tris(p-tolyl)phosphine, tris(m-tolyl)phosphine, tris(o-tolyl)phosphine, tris (p-methoxyphenyl)phosphine, tris(p-dimethylaminophenyl)phosphine, tricyclohexylphosphine, tricyclopentylphosphine, triethylphosphine, tri(1-naphthyl)phosphine, tribenzylphosphine, tri-n-butylphosphine, tri-t-butylphosphine.

Phosphites: trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl)phosphite, triphenyl phosphite, tris(2,4-di-t-butylphenyl)phosphite, tris(2-t-butyl-4-methoxyphenyl) phosphite, tris(2-t-butyl-4-methylphenyl)-phosphite, tris(p-cresyl)phosphite. In addition, sterically hindered phosphite ligands as are described, inter alia, in EP-A-155,508, U.S. Pat. Nos. 4,668,651, 4,748,261, 4,769,498, 4,774,361, 4,835,299, 4,885,401, 5,059,710, 5,113,022, 5,179,055, 5,260,491, 5,264,616, 5,288,918, 5,360,938, EP-A-472,071, EP-A-518,241 and WO-A-97/20795 are also suitable ligands.

Phosphonites: methyldiethoxyphosphine, phenyldimethoxyphosphine, phenyldiphenoxyphosphine, 2-phenoxy-2H-dibenzo[c,e] [1,2]oxaphosphorin and its derivatives in which all or some of the hydrogen atoms have been replaced by alkyl and/or aryl radicals or halogen atoms, and also ligands as are described in WO-A-98/43935, JP-A-09-268152 and DE-A-198 10 794 and in the German Patent Applications DE-A-199 54 721 and DE-A-199 54 510.

Useful phosphinite ligands are described, inter alia, in U.S. Pat. No. 5,710,344, WO-A-95/06627, U.S. Pat. No. 5,360,938 or JP-A-07-082281. Examples are diphenyl(phenoxy)phosphine and its derivatives in which all or some of the hydrogen atoms have been replaced by alkyl and/or aryl radicals or halogen atoms, diphenyl(methoxy)phosphine and diphenyl(ethoxy)phosphine.

The phosphites or phosphite-metal complexes of the invention can be used in processes for the hydroformylation of olefins, preferably those having from 2 to 25 carbon atoms, to form the corresponding aldehydes. Here, preference is given to using phosphite complexes with metals of transition group 8 as catalyst precursors.

In general, from 1 to 500 mol, preferably from 1 to 200 mol, more preferably from 2 to 50 mol, of the phosphite of the invention are used per mol of metal of transition group 8. Fresh phosphite ligand can be added to the reaction at any point in time in order to keep the concentration of free ligand constant.

The concentration of the metal in the reaction mixture is in the range from 1 ppm to 1000 ppm, preferably in the range from 5 ppm to 300 ppm, based on the total weight of the reaction mixture.

The hydroformylation reactions carried out using the phosphites of the invention or the corresponding metal complexes are carried out by known methods as described, for example, in J. FALBE, "New Syntheses with Carbon Monoxide", Springer Verlag, Berlin, Heidelberg, N.Y., page 95 ff., (1980). The olefin compound(s) is (are) reacted in the presence of the catalyst with a mixture of CO and $H_2$ (synthesis gas) to form the aldehydes having one more carbon atom.

The reaction temperatures for a hydroformylation process using the phosphites or phosphite-metal complexes of the invention as catalyst are preferably in the range from 40° C. to 180° C., more preferably from 75° C. to 140° C. The pressures under which the hydroformylation proceeds are preferably 1–300 bar of synthesis gas, more preferably 10–64 bar. The molar ratio of hydrogen to carbon monoxide ($H_2$/CO) in the synthesis gas is preferably from 10/1 to 1/10, more preferably from 1/1 to 2/1.

The catalyst or the ligand is present as a homogeneous solution in the hydroformylation mixture comprising starting materials (olefins and synthesis gas) and products (aldehydes, alcohols, high boilers formed in the process). A solvent can be additionally used if desired.

Owing to their high molecular weight, the phosphites of the invention have a low volatility. They can therefore be separated off easily from the more volatile reaction products. They have a sufficiently good solubility in customary organic solvents.

The starting materials for the hydroformylation are olefins or mixtures of olefins which have from 2 to 25 carbon atoms and a terminal or internal C=C double bond. They can be linear, branched or have a cyclic structure and can also have a plurality of olefinically unsaturated groups. Examples are propene; 1-butene, cis-2-butene, trans-2-butene, isobutene, butadiene, mixtures of $C_4$-olefins; $C_5$-olefins such as 1-pentene, 2-pentene, 2-methyl-1-butene, 2-methyl-2-butene, 3-methyl-1-butene; $C_6$-olefins such as 1-hexene, 2-hexene, 3-hexene, the $C_6$-olefin mixture formed in the dimerization of propene (dipropene); $C_7$-olefins such as 1-heptene, further n-heptenes, 2-methyl-1-hexene, 3-methyl-1-hexene; $C_8$-olefins such as 1-octene, further n-octenes, 2-methylheptenes, 3-methylheptenes, 5-methyl-2-heptene, 6-methyl-2-heptene, 2-ethyl-1-hexene, the isomeric $C_8$-olefin mixture formed in the dimerization of butenes (dibutene); $C_9$-olefins such as 1-nonene, further n-nonenes, 2-methyloctenes, 3-methyloctenes, the $C_9$-olefin mixture formed in the trimerization of propene (tripropene); $C_{10}$-olefins such as n-decenes, 2-ethyl-1-octene; $C_{12}$-olefins such as n-dodecenes, the $C_{12}$-olefin mixture formed in the tetramerization of propene or the trimerization of butenes (tetrapropene or tributene), $C_{14}$-olefins such as n-tetradecenes, $C_{16}$-olefins such as n-hexadecenes, the $C_{16}$-olefin mixture formed in the tetramerization of butenes (tetrabutene) and also olefin mixtures prepared by cooligomerization of olefins having different numbers of carbon atoms (preferably from 2 to 4), if desired after separation into fractions having the same number or a similar number of carbon atoms by distillation. It is likewise possible to use olefins or olefin mixtures produced by the Fischer-Tropsch synthesis and also olefins which are obtained by oligomerization of ethene or are obtainable via methathesis reactions or telomerization reaction.

Preferred starting materials are α-olefins in general, e.g. propene, 1-butene, 2-butene, 1-hexene, 1-octene and also dimers and trimers of butene (dibutene, di-n-butene, diisobutene, tributene).

The hydroformylation can be carried out continuously or batchwise. Examples of industrial apparatuses are stirred vessels, bubble columns, jet nozzle reactors, tube reactors and loop reactors, some of which may be cascaded and/or provided with internals.

The reaction can be carried out in one or more steps. The separation of the aldehyde compounds formed and the catalyst can be carried out by a conventional method, e.g. fractionation. Industrially, this can be achieved, for example, by means of a distillation, by means of a falling film evaporator or a thin film evaporator. This is particularly useful when a solution of the catalyst in a high-boiling solvent is separated from the lower-boiling products. The catalyst solution which has been separated off can be used for further hydroformylations. When lower olefins (e.g. propene, butene, pentene) are used, it is also possible for the products to be discharged from the reactor via the gas phase.

The following examples illustrate the present invention.

EXAMPLES

All examples were carried out under protective gas using standard Schlenk techniques. The solvents were dried over suitable desiccants before use.

Chloro Compound A

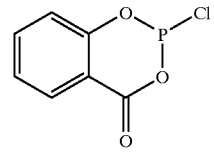

Chloro compound A (2-chloro-4H-1,3,2-benzodioxaphosphorin-4-one) was procured from Aldrich, Taufkirchen, and used as supplied.

Chloro Compound B

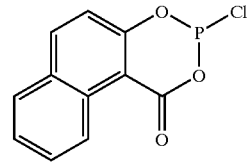

Chloro compound B was prepared from 2-hydroxy-1-naphthalenecarboxylic acid using a method based on that in BE 667036, Farbwerke Hoechst AG, 1966; Chem. Abstr. 65 (1966) 13741d. The following description explains the procedure for the synthesis:

Reaction of 2-hydroxy-1-naphthalenecarboxylic acid with Phosphorus Trichloride 9.22 g (0.049 mmol) of 2-hydroxy-1-naphthalenecarboxylic acid, 200 ml of dried toluene and 0.48 g (0.005 mol) of N-methyl-2-pyrrolidinone are placed in a 250 ml Schlenk tube. 10.14 g (0.073 mol) of phosphorus trichloride are slowly added to this mixture while stirring. After the Schlenk tube has been connected to an offgas line provided with a gas flowmeter, the reaction mixture is carefully heated to 95° C. and maintained at this temperature for 5 hours. For the work-up, the reaction mixture is filtered and the solvent of the filtrate is removed under reduced pressure.

Yield: 11.01 g (44.6 mmol), corresponding to 91.0% of theory.

$^{31}$P-NMR (toluene-D$_8$): δ 150.9 ppm

Preparation of calix[4]arene bis(O-acyl Phosphite) 1 (Mixture of Diastereomers)

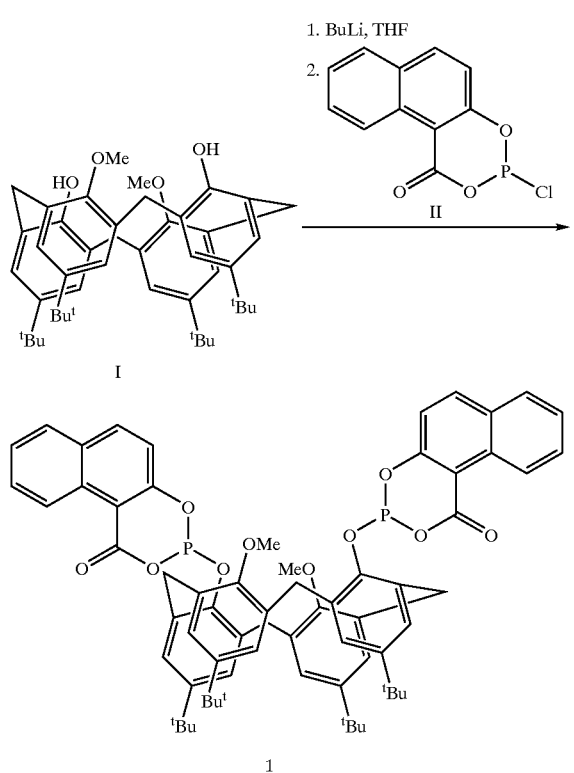

1.85 ml of a solution of n-butyllithium (1.6 mol/l, 2.96 mmol) in hexane was slowly added at room temperature to a solution of 1.0 g (1.48 mmol) of p-tert-butylbisdimethoxycalix[4]arene I in 40 ml of THF. The resulting solution was stirred at RT for 2 hours. 0.75 g (2.96 mmol) of 3-chloro-2,4-dioxa-3-phosphaphenanthren-1-one II dissolved in 5 ml of THF was subsequently added dropwise via a needle. A color change from colorless to yellowish occurred after the addition was complete. The solution was stirred overnight. Evaporation of the solvent gave crude bisphosphite 1 as a yellow solid. The product was purified by dissolution in 30 ml of CH$_2$Cl$_2$ and filtration through Celite® kieselguhr filter aid. Evaporation of the solution at 50° C. gave 1 as a yellowish air- and moisture-sensitive solid.

Yield: 1.24 g (1.26 mmol, 85%):

m.p. 278° C.

$^1$H-NMR in CDCl$_3$ (400.1 MHz): □=0.51 (s, 18 H, C(CH$_3$)$_3$); 0.53 (s, 18 H, C(CH$_3$)$_3$); 0.92 (s, 18 H, C(CH$_3$)$_3$); 0.95 (s, 18 H, C(CH$_3$)$_3$); 3.10 (d, 4 H, $^2$J(HH)=12.8 Hz, Ar—CH$_2$—Ar); 3.11 (d, 4 H, $^2$J(HH)=13.0 Hz, Ar—CH$_2$—Ar); 3.68 (s, 6 H, O—CH$_3$); 3.73 (s, 6 H, O—CH$_3$); 4.26 (d, 4 H, $^2$J(HH)=12.4 Hz, Ar—CH$_2$—Ar); 4.35 (d, 4H, $^2$J(HH)=12.8 Hz, Ar—CH$_2$—Ar); 6.11 (d, 2H, $^4$J(HH)=2.4 Hz, Ar—H); 6.13 (d, 2H, $^4$J(HH)=2.3 Hz, Ar—H); 6.38 (d, 2 H, $^4$J(HH)=2.3 Hz, Ar—H); 6.42 (d, 2 H, $^4$J(HH)=2.2 Hz, Ar—H); 6.55 (d, 2 H, $^4$J(HH)=2.2 Hz, Ar—H; 6.62 (d, 2 H, $^4$J(HH)=2.3 Hz, Ar—H); 6.63 (d, 4 H, $^4$J(HH)=2.3 Hz, Ar—H); 7.07–7.88 (m, 20 H, naph-H); 8.96 (d, 2 H, $^3$J(HH)=8.0 Hz, naph-H); 8.99 (d, 2 H, $^3$J(HH)=7.9 Hz, naph-H), $^{13}$C-NMR in CDCl$_3$ (100.6 MHz): □=30.48 (s, 6 C, C(CH$_3$)$_3$); 30.66 (s, 6 C, C(CH$_3$)$_3$); 31.30 (s, 6 C, C(CH$_3$)$_3$); 31.33 (s, 6 C, C(CH$_3$)$_3$); 32.06 (s, 4 C, Ar—CH$_2$—Ar); 32.10 (s, 4 C, Ar—CH$_2$—Ar); 33.82 (s, 2 C, C(CH$_3$)$_3$); 33.84 (s, 2 C, C(CH$_3$)$_3$); 33.85 (s, 2 C, C(CH$_3$)$_3$); 33.87 (s, 2 C, C(CH$_3$)$_3$); 61.01 (s, 2 C, O—CH$_3$); 61.28 (s, 2 C, O—CH$_3$); 118.49 (s, 4 C, naph-C); 124.79–129.50 (m, 40 C, Ar—C and naph-C); 129.87–146.21 (m, 48 C, Ar—C$_{quart.}$ and naph-C$_{quart.}$).

$^{31}$P-NMR in CDCl$_3$ (81.0 MHz): □=102.3, 103.5, 104.1, 104.6.

EI-MS, m/z (%): 1108 (4) [M]$^+$; 892 (5) [M+H–R]$^+$; 675 (50) [M–2 R]$^+$.

Elemental analysis:

C$_{68}$H$_{70}$O$_{10}$P$_2$ (1109.25) calc. C 73.63 H 6.36 P 5.58 found: C 70.13 H 6.37 P 5.30

Hydroformylation of 1-octene using calix[4]arene bis-O-acyl phosphite) 1

The hydroformylations were carried out in a Buddeberg 200 ml autoclave provided with pressure maintenance valve, gas flow meter and sparging stirrer. The autoclave was charged under an argon atmosphere with 10 ml of a 0.604 mM solution of rhodium in the form of [Rh(1.5-cyclooctadiene)acac] (acac=acetyl acetonate anion) as catalyst precursor, 5 ml of toluene as GC standard and the appropriate amounts of THF and calix[4]arene bis(O-acylphosphite) 1. 15 ml of 1-octene were placed in the pressure pipette. The total volume of the reaction solution was 56 ml. After replacement of the argon atmosphere by flushing with synthesis gas (CO/H$_2$ 1:1) the rhodium/ligand mixture was heated to 100 or 120° C. while stirring (1500 rpm) under a synthesis gas pressure of 30–33 bar. When the desired reaction temperature had been reached, the synthesis gas pressure was increased to 40 or 50 bar and kept constant by means of a pressure regulator during the entire reaction time. After addition of the olefin, the gas consumption was recorded by means of a Hitec gas flowmeter from Bronkhorst (NL). The reaction time for each of the hydroformylation experiments was 3 hours. The reaction mixture was subsequently cooled to room temperature, the autoclave was vented and flushed with argon. 2 ml of the autoclave solution were admixed with 10 ml of pentane and analyzed by gas chromatography; no olefin hydrogenation or alcohol formation were detected in the analysis.

TABLE 1

Hydroformylation of 1-octene

| Molar ratio of Rh:bis-phosphite | Yield [mol %] | C$_9$-aldehydes, total, of which [mol %] | Straight-chain C$_9$-aldehyde n-C9 [mol %] | Branched C$_9$-aldehydes | | | n/iso [mol %] |
|---|---|---|---|---|---|---|---|
| | | | | i-C8 [mol %] | i-C7 [mol %] | i-C6 [mol %] | |
| 1:1 | 83.3 | 53.4 | 35.1 | 7.3 | 4.2 | 1.15 | |
| 1:2 | 85.4 | 58.9 | 34.0 | 5.0 | 2.1 | 1.43 | |
| 1:10 | 46.0 | 59.2 | 39.0 | 1.5 | 0.3 | 1.45 | | n-C9 = nonanal
i-C8 = 2-methyloctanal
i-C7 = 2-ethylheptanal
i-C6 = 2-propylhexanal
n/iso = Ratio of nonanal/sum of all branched C$_9$-aldehydes.

What is claimed is:

1. A phosphite of the formula I,

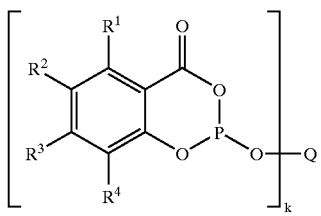

(I)

where $R^1$, $R^2$, $R^3$ and $R^4$ are each independently a monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I, $-CF_3$, $-CH_2(CF_2)_jCF_3$ where j=0–9, $-OR^9$, $-COR^9$, $-CO_2R^9$, $-CO_2M$, $-SR^9$, $-SO_2R^9$, $-SO_3R^9$, $-SO_3M$, $-SO_2NR^9R^{10}$, $-NR^9R^{10}$, or $-N=CR^9R^{10}$, where $R^9$ and $R^{10}$ are independently a H, monovalent substituted or unsubstituted aliphatic and aromatic hydrocarbon radical having from 1 to 25 carbon atoms and M is an alkali metal ion, an alkaline earth metal ion, an ammonium ion or a phosphonium ion, or adjacent radicals $R^1$ to $R^4$ together form a fused substituted or unsubstituted aromatic, heteroaromatic, aliphatic, mixed aromatic-aliphatic or mixed heteroaromatic-aliphatic ring system;

Q is a k-valent substituted or unsubstituted aliphatic, alicyclic, mixed aliphatic-alicyclic, aromatic, heteroaromatic, or mixed aliphatic-aromatic hydrocarbon radical having from 1 to 50 carbon atoms, where aliphatic parts of Q may contain one or more of oxygen, sulfur or nitrogen, k is at least 2 and $R^1$, $R^2$, $R^3$ and $R^4$ in the individual structural elements bound to Q can be different from one another.

2. The phosphite as claimed in claim 1, wherein at least two adjacent radicals $R^1$ to $R^4$ together form a fused aromatic, heteroaromatic, aliphatic, mixed aromatic-aliphatic or mixed heteroaromatic-aliphatic ring system which is unsubstituted or is substituted by at least one radical selected from among aliphatic, alicyclic, aromatic, heteroaromatic, mixed aliphatic-alicyclic, mixed aliphatic-aromatic, heterocyclic, mixed aliphaticheterocyclic hydrocarbon radicals having from 1 to 50 carbon atoms, F, Cl, Br, I, $-CF_3$, $-CH_2(CF_2)_jCF_3$ where j=0–9, $-OR^9$, $-COR^9$, $-CO_2R^9$, $-CO_2M$, $-SR^9$, $-SO_2R^9$, $-SOR^9$, $-SO_3R^9$, $-SO_3M$, $-SO_2NR^9R^{10}$, $-NR^9R^{10}$ or $-N=CR^9R^{10}$.

3. The phosphite as claimed in claim 1, wherein Q is a divalent hydrocarbon radical of the formula III

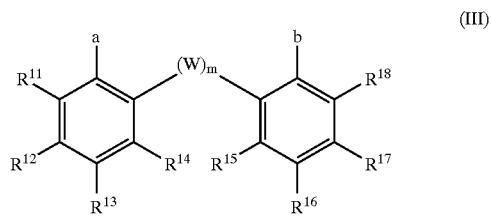

(III)

and $R^{11}$, $R^{12}$, $R^{13}$, $R^{14}$, $R^{15}$, $R^{16}$, $R^{17}$ and $R^{18}$ are each independently a monovalent substituted or unsubstituted aliphatic, alicyclic, aromatic, heteroatomic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I, $-CF_3$, $-CH_2(CF_2)_jCF_3$ where j=0–9, $-OR^9$, $-COR^9$, $-CO_2R^9$, $-CO_2M$, $-SR^9$, $-SO_2R^9$, $-SO_3R^9$, $-SO_3M$, $-SO_2NR^9R^{10}$, $-NR^9R^{10}$, or $-N=CR^9R^{10}$ where $R^9$ and $R^{10}$ are independently a H, monovalent substituted or unsubstituted aliphatic and aromatic hydrocarbon radical having from 1 to 25 carbon atoms and M is an alkali metal ion, an alkaline earth metal ion, an ammonium ion or a phosphonium ion, W is the divalent radical $CR^{19}R^{20}$, where $R^{19}$ and $R^{20}$ are as defined for $R^9$ and $R^{10}$, m=0–1 and the positions a and b represent the linkage points.

4. The phosphite as claimed in claim 1, wherein Q is a calix[n]arene radical of the formula IV

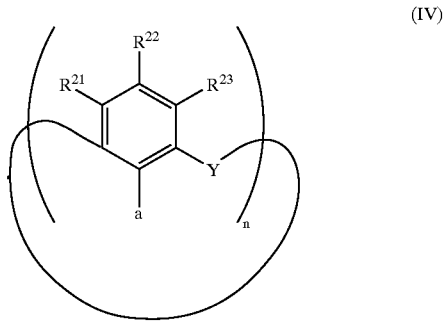

(IV)

where $R^{21}$, $R^{22}$ and $R^{23}$ are independently a substituted or unsubstituted aliphatic and aromatic hydrocarbon radical having from 1 to 25 carbon atoms, H, F, Cl, Br, I, $-CF_3$, $-CH_2(CF_2)_jCF_3$ where j=0–9, $-OR^{24}$, $-COR^{24}$, $-CO_2R^{24}$, $-CO_2M$, $-SR^{24}$, $-SO_2R^{24}$, $-SOR^{24}$, $-SO_3R^{24}$, $-SO_3M$, $-SO_2NR^{24}R^{25}$, $-NR^{24}R^{25}$, $-N=CR^{24}R^{25}$, where $R^{24}$ and $R^{25}$ are independently a H, monovalent substituted or unsubstituted aliphatic and aromatic hydrocarbon radical having from 1 to 25 carbon atoms and M is an alkali metal ion, an alkaline earth metal ion, an ammonium ion or a phosphonium ion, or adjacent radicals $R^{21}$ to $R^{23}$ together form a fused substituted or unsubstituted aromatic, heteroaromatic, aliphatic, mixed aromaticaliphatic or mixed heteroaromatic-aliphatic ring system;

Y is the divalent radical $CR^{24}R^{25}$ or $CR^{24}R^{25}$—O—$CR^{24}R^{25}$, n=3–6 and the positions a represent the linkage points or are occupied by $OR^{24}$, where $R^{24}$ and $R^{25}$ are as defined above.

5. A phosphite-metal complex comprising a metal of group 4, 5, 6, 7, 8, 9 or 10 of the Periodic Table of the Elements and one or more phosphites as claimed in claim 1.

6. The phosphite-metal complex as claimed in claim 5, wherein the metal is rhodium, platinum, palladium, cobalt or ruthenium.

7. A process for the hydroformylation of olefins, which comprises reacting a monoolefin or monoolefin mixture with a mixture of carbon monoxide and hydrogen in the presence of a phosphite-metal complex as claimed in claim 5.

8. A process for preparing a phosphite as claimed in claim 1, which comprises (a) reacting an α-hydroxyarylcarboxylic acid of the formula (1)

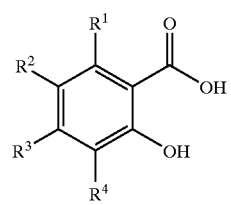

with $PCl_3$, $PBr_3$ or $PI_3$ in the presence of a base to form a halodioxaphosphorinone of the formula (2),

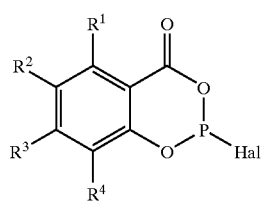

where Hal=Cl, Br or I, and (b) reacting the halodioxaphosphorinone (2) in the presence of a base with (i) a diol HO-Q-OH to give a phosphite of the formula (I), or (ii) a dicarboxylic acid HOOC-Q-COOH to give a phosphite of the formula (II).

9. The process for preparing a phosphite as claimed in claim 8, wherein two differently substituted halodioxaphosphorinones (2a) and (2b) are synthesized in (a) and are then reacted in succession with a diol in (b) (i) or reacted in succession with a dicarboxylic acid in (b) (ii) to give an unsymmetrical phosphite.

10. A process for preparing a phosphite-metal complex as claimed in claim 5, which comprises reacting a metal of group 4, 5, 6, 7, 8, 9 or 10 of the Periodic Table in elemental form or in the form of a chemical compound with the phosphite of formula (I).

11. A catalyst comprising the phosphite as claimed in claim 1.

12. A homogeneous catalyst comprising the phosphite as claimed in claim 1.

13. A hydroformylation catalyst comprising the phosphite as claimed in claim 1.

14. A hydroformylation catalyst comprising the phosphite metal complex as claimed in claim 5.

15. The process as claimed in claim 7 wherein the reacting is carried out in the presence of one or more additional phosphorous-containing ligands.

16. A phosphite of the formula II,

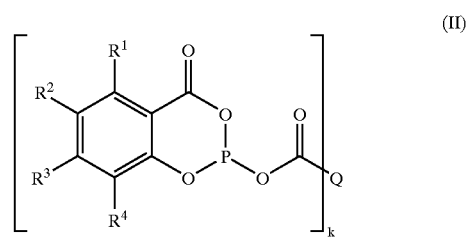

where $R^1$, $R^2$, $R^3$ and $R^4$ are each independently a monovalent substituted or unsubstituted aliphatic, alicyclic, aromatic, heteroatomic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SO_3R^9$, —$SO_3M$, —$SO_2NR^9R^{10}$, —$NR^9R^{10}$, or —$N=CR^9R^{10}$, where $R^9$ and $R^{10}$ are independently a H, monovalent substituted or unsubstituted aliphatic and aromatic hydrocarbon radical having from 1 to 25 carbon atoms and M is an alkali metal ion, an alkaline earth metal ion, an ammonium ion or a phosphonium ion, or adjacent radicals $R^1$ to $R^4$ together form a fused substituted or unsubstituted aromatic, heteroaromatic, aliphatic, mixed aromatic-aliphatic or mixed heteroaromatic-aliphatic ring system;

Q is a k-valent substituted or unsubstituted aliphatic, alicyclic, mixed aliphatic-alicyclic, heterocyclic, aromatic, heteroaromatic, or mixed aliphatic-aromatic hydrocarbon radical having from 1 to 50 carbon atoms, where aliphatic parts of Q may contain one or more of oxygen, sulfur or nitrogen, k is at least 2 and $R^1$, $R^2$, $R^3$ and $R^4$ in the individual structural elements bound to Q can be different from one another.

17. The phosphite as claimed in claim 16, wherein at least two adjacent radicals $R^1$ to $R^4$ together form a fused aromatic, heteroaromatic, aliphatic, mixed aromatic-aliphatic or mixed heteroaromatic-aliphatic ring system which is unsubstituted or is substituted by at least one radical selected from among aliphatic, alicyclic, aromatic, heteroaromatic, mixed aliphatic-alicyclic, mixed aliphatic-aromatic, heterocyclic, mixed aliphatic heterocyclic hydrocarbon radicals having from 1 to 50 carbon atoms, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SOR^9$, —$SO_3R^9$, —$SO_3M$, —$SO_2NR^9R^{10}$, —$NR^9R^{10}$ or —$N=CR^9R^{10}$.

18. The phosphite as claimed in claim 16, wherein Q is a divalent hydrocarbon radical of the formula III

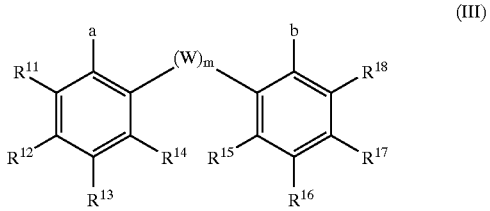

(III)

and $R^{11}$, $R^{12}$, $R^{13}$, $R^{14}$, $R^{15}$, $R^{16}$, $R^{17}$ and $R^{18}$ are each independently a monovalent substituted or unsubstituted aliphatic, alicyclic, aromatic, heteroatomic, mixed aliphatic-alicyclic, mixed aliphatic-aromatic, heterocyclic, mixed aliphatic-heterocyclic hydrocarbon radical having from 1 to 50 carbon atoms, H, F, Cl, Br, I, —$CF_3$, —$CH_2(CF_2)_jCF_3$ where j=0–9, —$OR^9$, —$COR^9$, —$CO_2R^9$, —$CO_2M$, —$SR^9$, —$SO_2R^9$, —$SO_3R^9$, —$SO_3M$, —$SO_2NR^9R^{10}$, —$NR^9R^{10}$, or —$N{=}CR^9R^{10}$ where $R^9$ and $R^{10}$ are independently a H, monovalent substituted or unsubstituted aliphatic and aromatic hydrocarbon radical having from 1 to 25 carbon atoms and M is an alkali metal ion, an alkaline earth metal ion, an ammonium ion or a phosphonium ion, W is the divalent radical $CR^{19}R^{20}$, where $R^{19}$ and $R^{20}$ are as defined for $R^9$ and $R^{10}$, m=0–1 and the positions a and b represent the linkage points.

19. The phosphite as claimed in claim 16, wherein Q is a calix[n]arene radical of the formula IV

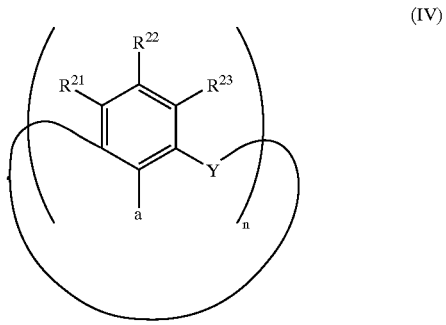

(IV)

where $R^{21}$, $R^{22}$ and $R^{23}$ are independently a substituted or unsubstituted aliphatic and aromatic hydrocarbon radical having from 1 to 25 carbon atoms, H, F, Cl, Br, I, —$CF_3$, —$CH_2(CF_2)_jCF_3$ where j=0–9, —$OR^{24}$, —$COR^{24}$, —$CO_2R^{24}$, —$CO_2M$, —$SR^{24}$, —$SO_2R^{24}$, —$SOR^{24}$, —$SO_3R^{24}$, —$SO_3M$, —$SO_2NR^{24}R^{25}$, —$NR^{24}R^{25}$, —$N{=}CR^{24}R^{25}$, where $R^{24}$ and $R^{25}$ are $R^9$ and $R^{10}$ are independently a H, monovalent substituted or unsubstituted aliphatic and aromatic hydrocarbon radical having from 1 to 25 carbon atoms an alkaline and M is an alkali metal ion, an alkaline earth metal ion, an ammonium ion or a phosphonium ion, or adjacent radicals $R^{21}$ to $R^{23}$ together form a fused substituted or unsubstituted aromatic, heteroaromatic, aliphatic, mixed aromatic aliphatic or mixed heteroaromatic-aliphatic ring system;

Y is the divalent radical $CR^{24}R^{25}$ or $CR^{24}R^{25}$—O—$CR^{24}R^{25}$, n=3–6 and the positions a represent the linkage points or are occupied by $OR^{24}$, where $R^{24}$ and $R^{25}$ are as defined above.

20. A phosphite-metal complex comprising a metal of group 4, 5, 6, 7, 8, 9 or 10 of the Periodic Table of the Elements and one or more phosphites as claimed in claim 16.

21. The phosphite-metal complex as claimed in claim 5, wherein the metal is rhodium, platinum, palladium, cobalt or ruthenium.

22. The phosphite-metal complex as claimed in claim 20, wherein the metal is rhodium, platinum, palladium, cobalt or ruthenium.

23. A process for the hydroformylation of olefins, which comprises reacting a monoolefin or monoolefin mixture with a mixture of carbon monoxide and hydrogen in the presence of a phosphite-metal complex as claimed in claim 20.

24. A process for preparing a phosphite as claimed in claim 16, which comprises (a) reacting an α-hydroxyarylcarboxylic acid of the formula (1)

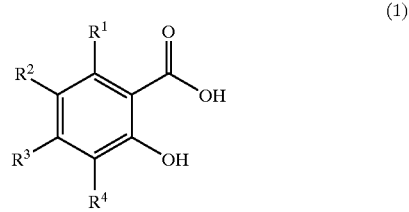

(1)

with $PCl_3$, $PBr_3$ or $PI_3$ in the presence of a base to form a halodioxaphosphorinone of the formula (2),

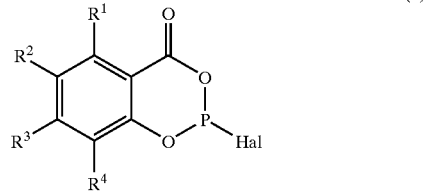

(2)

where Hal=Cl, Br or I, and (b) reacting the halodioxaphosphorinone (2) in the presence of a base with (i) a diol HO-Q-OH to give a phosphite of the formula (I), or (ii) a dicarboxylic acid HOOC-Q-COOH to give a phosphite of the formula (II).

25. The process for preparing a phosphite as claimed in claim 24, wherein two differently substituted halodioxaphosphorinones (2a) and (2b) are synthesized in (a) and are then reacted in succession with a diol in (b) (i) or reacted in succession with a dicarboxylic acid in (b) (ii) to give an unsymmetrical phosphite.

26. A process for preparing a phosphite-metal complex as claimed in claim 20, which comprises reacting a metal of group 4, 5, 6, 7, 8, 9 or 10 of the Periodic Table in elemental form or in the form of a chemical compound with the phosphite of formula (I).

27. A catalyst comprising the phosphite as claimed in claim 16.

28. A homogeneous catalyst comprising the phosphite as claimed in claim 20.

29. A hydroformylation catalyst comprises the phosphite as claimed in claim 16.

30. A hydroformylation catalyst comprising the phosphite metal complex as claimed in claim 20.

* * * * *